| (12) | United States Patent | (10) Patent No.: | US 9,066,763 B2 |
|---|---|---|---|
| | Khoo et al. | (45) Date of Patent: | Jun. 30, 2015 |

(54) SURGICAL INSTRUMENT WITH INTEGRATED REDUCTION AND DISTRACTION MECHANISMS

(75) Inventors: Larry T. Khoo, Studio City, CA (US); Peter Thomas Miller, Austin, TX (US); Ryan Carter Harvey, Bordeaux (FR); Craig Lee Ford, Beverly Hills, CA (US)

(73) Assignee: Zimmer Spine, Inc., Minneapolis, MN (US)

(*) Notice: Subject to any disclaimer, the term of this patent is extended or adjusted under 35 U.S.C. 154(b) by 1523 days.

(21) Appl. No.: 12/183,967

(22) Filed: Jul. 31, 2008

(65) Prior Publication Data

US 2010/0024487 A1 Feb. 4, 2010

(51) Int. Cl.
  *A61B 17/70* (2006.01)
  *A61B 17/60* (2006.01)
  *A61B 17/02* (2006.01)

(52) U.S. Cl.
  CPC ......... *A61B 17/7091* (2013.01); *A61B 17/7077* (2013.01); *A61B 17/7079* (2013.01); *A61B 17/60* (2013.01); *A61B 17/708* (2013.01); *A61B 2017/0256* (2013.01); *A61B 17/7086* (2013.01)

(58) Field of Classification Search
  CPC ............ A61B 17/7074–17/7091; A61B 17/60; A61B 17/708
  USPC .................. 606/246–279, 86 A, 105
  See application file for complete search history.

(56) References Cited

U.S. PATENT DOCUMENTS

| 4,898,161 A | 2/1990 | Grundei |
| 6,090,113 A | 7/2000 | Le Couedic et al. |
| 6,530,929 B1 | 3/2003 | Justis et al. |

(Continued)

FOREIGN PATENT DOCUMENTS

| DE | 10125717 | 12/2002 |
| EP | 0528177 A2 | 2/1993 |

(Continued)

OTHER PUBLICATIONS

International Search Report and Written Opinion dated Feb. 10, 2009 in International Application No. PCT/US2009/046567, 16 pages.

(Continued)

*Primary Examiner* — Jerry Cumberledge
*Assistant Examiner* — Nicholas Plionis
(74) *Attorney, Agent, or Firm* — Seager, Tufte & Wickhem LLC

(57) ABSTRACT

Embodiments of a surgical instrument disclosed herein can include mechanisms for reduction and distraction as well as compression. Some embodiments of the surgical instrument may comprise a reducer knob having a first passage through which a first shaft of a driver is acceptable, a connecting element coupled to the reducer knob and having a second passage through which the first shaft of the driver is acceptable, a compressor handle coupled to the connecting element at a first end and having a through hole, and a common handle coupled to the compressor handle via the through hole and pivots between the reducer knob and the compressor handle. With embodiments of a surgical instrument disclosed herein, surgical personnel can distract and hold vertebrae in a distracted state and perform a reduction without having to switch or add instruments. Some embodiments disclosed herein can be particularly useful for reducing spondylolisthesis during posterior fixation.

23 Claims, 11 Drawing Sheets

(56) References Cited

U.S. PATENT DOCUMENTS

| | | | |
|---|---|---|---|
| 6,669,699 | B2 | 12/2003 | Ralph et al. |
| 6,716,218 | B2 | 4/2004 | Holmes et al. |
| 6,740,087 | B2 | 5/2004 | Knox |
| 6,926,718 | B1 | 8/2005 | Michaelson |
| 7,004,947 | B2 | 2/2006 | Shluzas et al. |
| 7,008,432 | B2 | 3/2006 | Schlapfer et al. |
| 7,160,300 | B2 | 1/2007 | Jackson |
| 7,250,052 | B2 | 7/2007 | Landry et al. |
| 7,811,288 | B2 | 10/2010 | Jones et al. |
| 2002/0161368 | A1 | 10/2002 | Foley et al. |
| 2003/0187453 | A1 | 10/2003 | Schlapfer et al. |
| 2004/0138662 | A1 | 7/2004 | Landry et al. |
| 2004/0143265 | A1 | 7/2004 | Landry et al. |
| 2004/0172022 | A1 | 9/2004 | Landry et al. |
| 2006/0036244 | A1 | 2/2006 | Spitler |
| 2006/0036255 | A1 | 2/2006 | Pond, Jr. et al. |
| 2006/0084993 | A1 | 4/2006 | Landry et al. |
| 2006/0095035 | A1 | 5/2006 | Jones et al. |
| 2006/0111713 | A1* | 5/2006 | Jackson ............... 606/61 |
| 2006/0122597 | A1* | 6/2006 | Jones et al. .......... 606/61 |
| 2006/0142761 | A1 | 6/2006 | Landry et al. |
| 2006/0149278 | A1 | 7/2006 | Abdou |
| 2006/0217735 | A1 | 9/2006 | MacDonald et al. |
| 2006/0235427 | A1 | 10/2006 | Thomas et al. |
| 2006/0247630 | A1* | 11/2006 | Iott et al. ............. 606/61 |
| 2006/0247645 | A1 | 11/2006 | Wilcox et al. |
| 2006/0247649 | A1 | 11/2006 | Rezach et al. |
| 2007/0239159 | A1 | 10/2007 | Altarac et al. |
| 2008/0077155 | A1 | 3/2008 | Diederich et al. |
| 2010/0004695 | A1* | 1/2010 | Stad et al. ............ 606/86 A |

FOREIGN PATENT DOCUMENTS

| | | |
|---|---|---|
| EP | 528177 A2 * | 2/1993 |
| WO | WO 2005107415 | 11/2005 |
| WO | WO 2006060430 | 6/2006 |
| WO | WO2006091863 A2 | 8/2006 |

OTHER PUBLICATIONS

Setti S. Rengachary, M.D. and Raju Balabhandra, M.D. "Reduction of Spondylolisthesis" Neurosurg Focus, vol. 13 (1):Article 2, Jul. 2002, pp. 1-3.

Sylvain Palmer, M.D. et al. "Bilateral Decompressive Surgery in Lumbar Spinal Stenosis Associated with . . . " Neurosurg Focus, vol. 13 (1):Article 4, Jul. 2002, pp. 1-6.

Will Forest Beringer, D.O. et al. "Anterior Transvertebral Interbody Cage with Posterior Transdiscal Pedicle Screw . . . " Neurosug Focus, vol. 20 (3):E7, Mar. 2006, pp. 1-7.

Giovanni La Rosa, M.D., et al. "Posterior Fusion and Implantation of the SOCON-SRI System in the Treatment of . . . " Neurosurg Focus, Vo. 7 (6):Article 2, 1999, 11 pages.

Jeffrey A. Kozak, M.D. "Discussion: Isthmic Spondylolisthesis . . . ?" SpineUniverse, 3 pgs [downloaded from the Internet on Jun. 2, 2008, <<URL:http//www.spineuniverse.com/>>.

"System Designed to Simplify the Correction of Spinal Deformities . . . " Medical News Today, Jan. 27, 2007, [downloaded from the Internet Jun. 2, 2008, <<www.medicalnewstoday.com>>.

Office Action for U.S. Appl. No. 11/002,931, Jones et al., dated Jan. 10, 2008 (9 pages).

Office Action for U.S. Appl. No. 11/002,931, Jones et al., dated Dec. 16, 2008 (13 pages).

Office Action for U.S. Appl. No. 11/002,931, Jones et al., dated Jul. 21, 2009 (9 pages).

Office Action for U.S. Appl. No. 11/002,931, Jones et al., dated Jul. 15, 2008 (15 pages).

International Search Report for PCT/US2005/043199 dated Apr. 6, 2006 (4 pages).

International Preliminary Report on Patentability with Written Opinion of the International Searching Authority, PCT/US05/043199, Jun. 5, 2007, 7 pages.

Extended European Search Report issued for European Patent Application No. 10 005 583.9, completed on Sep. 16, 2010, mailed on Sep. 29, 2010, 7 pages.

Written Opinion issued for PCT Application No. PCT/US2005/043199, dated Apr. 6, 2006, 6 pgs.

International Preliminary Report on Patentability issued for PCT Application No. PCT/US2009/046567, issued on Feb. 1, 2011 and mailed on Feb. 10, 2011, 10 pgs.

* cited by examiner

SURGICAL INSTRUMENT WITH INTEGRATED REDUCTION AND DISTRACTION MECHANISMS

TECHNICAL FIELD OF THE DISCLOSURE

Embodiments of the disclosure relate generally to instruments for spine surgery. More particularly, embodiments of the disclosure relate to surgical instruments useful for treating spondylolisthesis. Even more particularly, embodiments disclosed herein relate to a surgical instrument with integrated reduction and distraction mechanisms.

BACKGROUND OF THE RELATED ART

The human spine consists of segments known as vertebrae linked by intervertebral disks and held together by ligaments. There are 24 movable vertebrae—7 cervical (neck) vertebrae, 12 thoracic (chest) vertebrae, and 5 lumbar (back) vertebrae. Each vertebra has a somewhat cylindrical bony body (centrum), a number of winglike projections (processes), and a bony arch. The arches are positioned so that the space they enclose forms the vertebral canal. The vertebral canal houses and protects the spinal cord, and within it the spinal fluid circulates. Ligaments and muscles are attached to various projections of the vertebrae. The bodies of the vertebrae form the supporting column of the skeleton. Fused vertebra make up the sacrum and coccyx, the very bottom of the vertebral column.

The spine is subject to abnormal curvature, injury, infections, tumor formation, arthritic disorders, and puncture or slippage of the cartilage disks. Modern spine surgery often involves the use of spinal stabilization/fixation procedures such as a vertebral body fusion procedure to correct or treat various acute or chronic spine disorders and/or to support the spine. In conjunction with these procedures, some spinal implants may be utilized to help stabilize the spine, correct deformities of the spine such as spondylolisthesis or pseudarthrosis, facilitate fusion, or treat spinal fractures. Some spinal implants such as a spinal fixation system may provide fused and/or rigid support for the affected regions of the spine. For example, a spinal fixation system may include a corrective spinal implant that is attached to selected vertebrae of the spine by screws, hooks, and clamps. The corrective spinal implant may include spinal rods or plates that are generally parallel to the patients back. The corrective spinal implant may also include transverse connecting rods that extend between neighboring spinal rods. Spinal fixation systems can be used to correct problems in the cervical, thoracic, and lumbar portions of the spine, and are often installed posterior to the spine on opposite sides of the spinous process and adjacent to the transverse process. Spinal fixation systems when implanted inhibit movement in the affected regions in virtually all directions.

More recently, so called "dynamic" systems have been introduced. Dynamic spinal stabilization systems can better match a patient's anatomy than some spinal stabilization systems used to provide static support. When implanted in a patient, a dynamic spinal stabilization system can allow at least some movement (e.g., flexion, extension, lateral bending, or torsional rotation) of the affected regions of the spine in at least some of the directions, giving the patient a greater range of motion. Dynamic stabilization systems can be used in scenarios in which vertebral body fusion is not desired, in which vertebral body (re)alignment is desired, and in which it is desired to support or strengthen degraded, diseased, damaged, or otherwise weakened portions of the spine.

Often, spinal stabilization systems include rods which can bear a portion of the forces that would otherwise be transmitted along the spine. These rods may be implanted in pairs or in other numbers along portions of the spine of interest. Some spinal stabilization systems may support a portion of the spine including only two vertebrae (and associated anatomical structures) while some spinal stabilization systems support portions of the spine extending beyond two vertebrae. Spinal stabilizations systems can be used to support various portions of the spine, including the lumbar portion of the spine and the thoracic portion of the spine. Regardless of the number of rods implanted, or the portion of the spine in which they may be implanted, the rods can be attached to one or more vertebrae of the spine to provide support and stabilize, align, or otherwise treat the region of the spine of interest. Surgical personnel may use one or more anchor systems to attach the rods to one or more vertebrae. One such anchor system includes pedicle screws constructs which define slots, keyways, grooves, apertures, or other features for accepting and retaining stabilization rods which may be static, dynamic, or a combination of both. In many pedicle screw constructs, pedicle screws are placed in vertebrae selected by surgical personnel.

During surgical procedures, sometimes a rod (or more than one rod) remains proud of its desired or final position in the rod slot of the screw head by some height or distance. Such scenarios include surgical procedures in which it is desired to anchor a rod to more than one vertebra. One such scenario can occur when pedicle screws have been implanted in two vertebrae and it is desired to anchor a rod to a third vertebra lying between the two vertebrae. In this, and other scenarios, a rod reduction instrument can be navigated to the implant site by surgical personnel to correct this situation by urging the rod into position in the pedicle screw. In some situations, the body of the rod reduction instrument may block the view of the surgical site. In other situations, the actuation handles of the instrument may rotate into the line of sight of the surgical personnel. Thus, as they attempt to reduce the rod into its desired position and lock the rod in place, surgical personnel sometimes cannot see portions of the surgical site and/or the spinal stabilization system being implanted. In some scenarios, reduced visibility of the implant site can result in slower, less efficient, and less accurate surgical results than desired. When the patient is abnormally large, the line of sight of the surgical personnel may be further impeded.

In some cases, particularly during certain surgical procedures, distraction of vertebrae may need to be performed prior to the reduction. For example, to treat spondylolisthesis, which is a slippage of one vertebral body on top of another, surgical personnel may need to use one or more instruments to hold the affected vertebrae apart or otherwise in a distracted state and then use another one or more instruments to perform a reduction on a slipped vertebral body and pull it back up in line with the rest of vertebrae. In some situations, surgical personnel may need to use additional instrumentation such as a compression instrument to adjust the distance between the vertebrae. Thus, during surgery, surgical personnel may need to use several instruments in order to perform distraction, compression, and reduction.

SUMMARY OF THE DISCLOSURE

Embodiments disclosed herein provide a surgical instrument that integrates multiple surgical functions, providing the surgical personnel a way to shorten the operating time and increase the efficiency and accuracy of surgical steps. Some embodiments of the surgical instrument disclosed herein include mechanisms for reduction and distraction. Some embodiments of the surgical instrument disclosed herein include mechanisms for reduction, distraction, and compression. Embodiments of the surgical instrument disclosed herein can allow surgical personnel to distract affected vertebrae, hold them in a distracted state, and perform a reduction to correct a spondylolisthesis without having to switch out one instrument for another. Some embodiments of the surgical instrument disclosed herein can be particularly useful for reducing difficult spondylolisthesis during posterior fixation.

In some embodiments, a surgical instrument with integrated mechanisms for reduction and distraction may comprise a reducer knob, a reducer tube coupled to the reducer knob, a connecting element coupled to the reducer knob and the reducer tube, a common handle pivotally coupled to the connecting element, and a shaft fixedly attached to or made part of the common handle. The reducer knob, the connecting element, and the reducer tube may have an inner diameter that accommodates a distractor handle, which, in one embodiment, may be the shaft of a driver such as a closure top driver. For distraction, a surgeon may squeeze the common handle and the distractor handle together, moving them toward one another. This motion increases a distance between the shaft of the common handle and the shaft of the distractor handle under the reducer tube. For reduction, the surgeon may turn the reducer knob to adjust a height of the reducer tube. One end of the reducer knob may have an inner diameter sufficiently large to accommodate an outer diameter of the reducer tube such that a portion of the reducer tube may be retracted into the reducer knob.

In some embodiments, the surgical instrument further includes a compressor handle coupled to the connecting element and the common handle. For compression, the surgeon may squeeze the common handle and the compressor handle together, moving them toward each other. This motion decreases the distance between the shaft of the common handle and the shaft of the distractor handle under the reducer tube. In some embodiments, the compressor handle has an L-shape. In some embodiments, the surgical instrument further comprises a dial coupled to the compressor handle and a pivot locking knob coupled to the common handle. In some embodiments, turning the dial adjusts a distance between the compressor handle and the common handle. In some embodiments, locking the pivot locking knob locks the distance between the compressor handle and the common handle.

In some embodiments, the reducer tube has cutouts to straddle a rod during reduction. In some embodiments, the inner diameter of the reducer tube car accommodate an extender sleeve. In some embodiments, the reducer tube has a non-threaded end for engaging a counter torque tube.

In some embodiments, the surgical instrument further comprises a pivot locking knob coupled to the common handle for locking the distance between the shaft of the common handle and the reducer tube and thus the shaft of the distractor handle.

In some embodiments, the surgical instrument may include a driver and the shaft of the driver is utilized as the distractor handle. According to some embodiments, the distractor handle and the common handle can be locked in a desired position during surgery to, for example, hold vertebrae in a distracted state. This can be done via various locking means. In some embodiments, the surgical instrument further comprises a locking mechanism having a first portion, a second portion, and a lock. The first portion and the second portion of the locking means can be attached to the distractor handle and the common handle and locked using the lock. In some embodiments, the locking mechanism is a surgical ratchet. In some embodiments, a ratchet arm is coupled to the common handle to ratchet with the distractor handle.

In some embodiments, a surgical instrument with integrated mechanisms for reduction, distraction, and compression comprises a reducer knob having a first passage through which a first shaft of a driver is acceptable, a connecting element coupled to the reducer knob and having a second passage through which the first shaft of the driver is acceptable, a compressor handle coupled to the connecting element at a first end and having a through hole, and a common handle coupled to the compressor handle via the through hole and pivots between the reducer knob and the compressor handle. In some embodiments, the compressor handle is vertically oriented and perpendicular to the connecting element. In some embodiments, the compressor handle has an L-shape.

In some embodiments, the through hole has an elongated shape that allows the common handle to travel a distance along a longitudinal axis. Further, a dial may be coupled to the compressor handle for adjusting the distance and a locking knob may be coupled to the common handle for locking the common handle at a desired position and angle. In some embodiments, a locking mechanism may be coupled to the common handle for locking the common handle at a desired position and angle.

In some embodiments, the common handle may have a second shaft such that moving the common handle towards the first shaft of the driver increases a distance between the shaft of the common handle and the shaft of the driver, which extends through the first and second passages. In some embodiments, a reducer tube may be coupled to the reducer knob and having a third passage through which the shaft of the driver is passable. The reducer knob and the reducer tube can work in concert such that turning the reducer knob in a first direction extends a height of the reducer tube and turning the reducer knob in a second direction retracts a portion of the reducer tube into the reducer knob. In some embodiments, the reducer tube may extend longitudinally over an extender sleeve which may be utilized in a minimally invasive procedure. In these embodiments, the reducer tube has an inner diameter that accommodates the extender sleeve and may have cutouts to straddle a rod. In some embodiments, the reducer tube does not extend over an extender sleeve. Instead, the reducer tube may have a diameter for pushing against a counter torque tube. In these embodiments, the reducer tube may have a non-threaded end for engaging the counter torque tube.

Some embodiments of a surgical instrument disclosed herein may have various features to reduce the weight, making it easier to handle. In some embodiments, the compressor handle of the surgical instrument may have one or more weight reducing windows. In some embodiments, the common handle of the surgical instrument may have one or more weight reducing windows. As one skilled in the art can appreciate, weight reducing windows, holes, cavities, recesses, and the like may be implemented at various non-structural portions of the surgical instrument.

In some embodiments, a surgical method may comprise moving a common handle of a surgical instrument towards a distractor handle of the surgical instrument to increase a distance between vertebral bodies anchoring bone fastener assemblies each of which, in turn, is coupled to a shaft of the surgical instrument, perhaps by way of an extender sleeve. The surgical instrument further comprises a reducer knob coupled to the distractor handle, a reducer tube coupled to the reducer knob, and a connecting element coupled to the reducer knob and the reducer tube. In some embodiments, the common handle is pivotally coupled to the connecting element. The surgical method may further comprise turning the reducer knob of the surgical instrument to extend a portion of the reducer tube out from the reducer knob to contact and press against a rod, pulling a bone fastener assembly up until a vertebral body anchoring the bone fastener assembly lines up with adjacent vertebrae. Some embodiments of the surgical method disclosed herein can be particularly useful for reducing spondylolisthesis.

Other objects and advantages of the embodiments disclosed herein will be better appreciated and understood when considered in conjunction with the following description and the accompanying drawings.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein.

Figure 1:
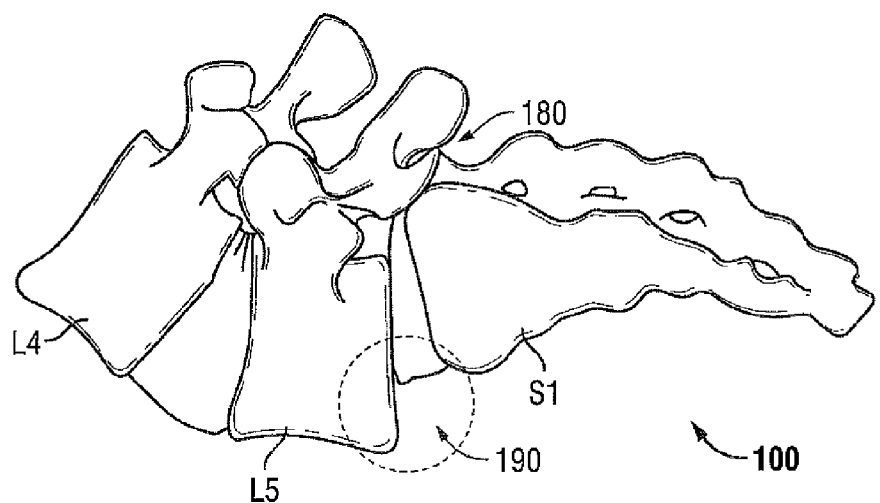
FIG. 1 depicts a portion of the spine with a slippage at L5-S1 level of the spine.

While this disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but to the contrary, the intention is to cover all modifications, equivalents and alternatives falling within the spirit and scope of the present disclosure as defined by the appended claims.

DETAILED DESCRIPTION

A surgical instrument for spinal stabilization systems and the various features and advantageous details thereof are explained more fully with reference to the non-limiting embodiments detailed in the following description. Descriptions of well known starting materials, manufacturing techniques, components and equipment are omitted so as not to unnecessarily obscure the invention in detail. Skilled artisans should understand, however, that the detailed description and the specific examples, while disclosing preferred embodiments of the invention, are given by way of illustration only and not by way of limitation. Various substitutions, modifications, and additions within the scope of the underlying inventive concept(s) will become apparent to those skilled in the art after reading this disclosure. Skilled artisans can also appreciate that the drawings disclosed herein are not necessarily drawn to scale.

As used herein, the terms "comprises," "comprising," includes, "including," "has," "having" or any other variation thereof, are intended to cover a non-exclusive inclusion. For example, a process, product, article, or apparatus that comprises a list of elements is not necessarily limited to only those elements, but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to a particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

Spondylolisthesis occurs when one vertebra slips forward on the adjacent vertebrae, which may results in irritation to the nerve and disc. FIG. 1 depicts a portion of spine 100 with slippage 190 at L5-S1 level of the spine. Such a slippage can occur at other levels of the spine such as L3-L4 and L4-L5. The degree of slippage can vary. In the example of FIG. 1, the slippage of L5 is quite severe and may require reduction surgery to pull it back up and realign it with the rest of the vertebrae.

Figures 2A, 2B:
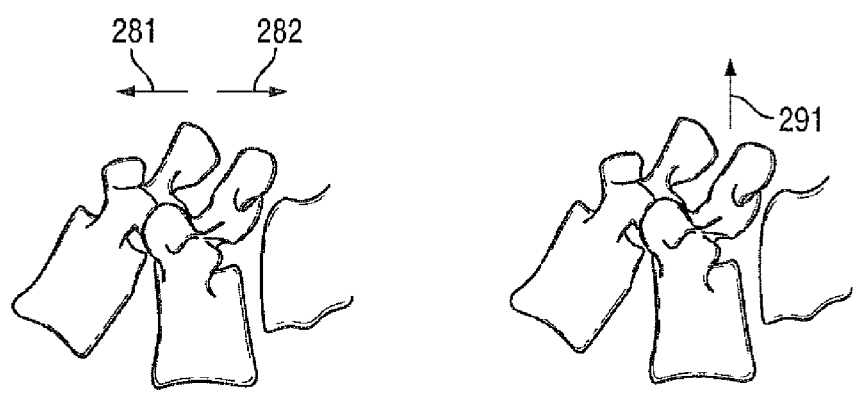
FIGS. 2A-2B depict a portion of the spine and show examples of distraction and reduction.

In some situations, surgical personnel may need to first clear a path to the slipped vertebra before a reduction can be performed to pull it back up. One such situation may be that a part or parts of the slipped vertebra is/are blocked by neighboring vertebra(e), making it difficult for surgical personnel to perform the reduction on the slipped vertebra. As an example, in FIG. 1, arrow 180 points to a part of an adjacent vertebra (S1) that is blocking a portion of the slipped vertebra (L5). Thus, to reduce L5 and bring it back up in line with L4 and S1, surgical personnel would need to first clear blockage or interference point 180. One way to clear interference point 180 is to increase a distance between L5 and S1. This can be done by distraction in one or both directions as indicated by arrows 281 and 282 in FIG. 2A. The distracted vertebrae can then be held in this distracted state while a reduction is performed on an affected vertebra in a direction as indicated by arrow 291 in FIG. 2B. Previously, to perform the above steps, surgical personnel would need to use several instruments to distract, hold, and reduce, perhaps switching out one instrument for another and repeating the steps when necessary.

Figure 3:
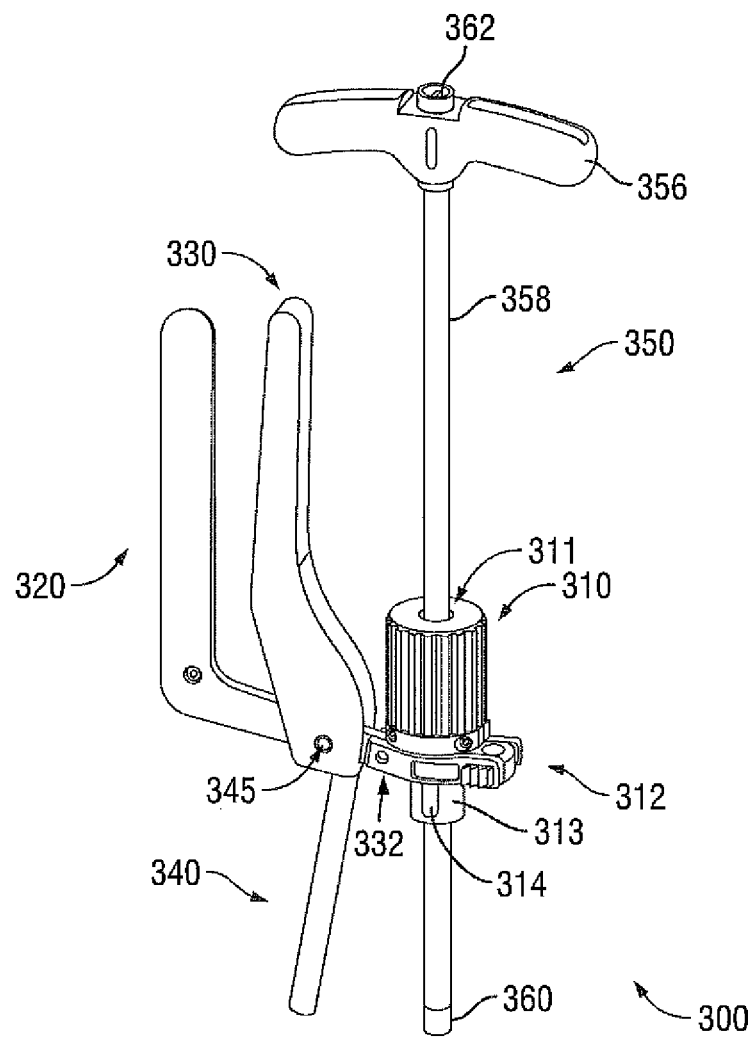
FIG. 3 depicts one embodiment of a surgical instrument with a distractor handle, a common handle, and a compressor handle.

FIG. 3 depicts one embodiment of surgical instrument 300 comprising distractor handle 358, common handle 330, and optionally compressor handle 320. Surgical instrument 300 integrates multiple mechanisms, including reduction, distraction, and optionally compression. Surgical instrument 300 thus may allow surgical personnel to distract affected vertebrae, hold them in a distracted state, and perform a reduction to correct a slipped vertebra without having to rely on multiple instruments such as a reducer, a distractor, and a compressor.

In the example shown in FIG. 3, the reduction assembly comprises reducer knob 310 and reducer tube 313 attached to rack or connecting element 312, all of which are aligned along a central axis of aperture 311 and have an inner diameter sufficiently large to allow a rod or shaft 358 to pass through. Additionally, aperture 311 may also allow targeting needles, tissue dilators, rod pushers (seaters), universal drivers, screw adjusters, bone awls, bone taps and the like to pass through as necessary during a spinal stabilization procedure. Examples of a spinal stabilization procedure and surgical instruments used therein, including targeting needles, tissue dilators, bone awls, and bone taps, are described in co-pending U.S. patent application Ser. No. 11/284,282, entitled "SPINAL STABILIZATION SYSTEMS AND METHODS," which is a continuation application of U.S. Pat. No. 7,250,052, entitled "SPINAL STABILIZATION SYSTEMS AND METHODS," the contents of which are incorporated herein as if set forth in full. As one skilled in the art can appreciate, other tools and instruments with a long shaft may also be able to pass through aperture 311 and be used as distractor handle 358 of surgical instrument 300.

In some embodiments, distractor handle 358 may be part of driver 350. In one embodiment, driver 350 is a locking driver. In one embodiment, driver 350 is a T-handle driver. In one embodiment, driver 350 is a closure top driver having handle 356, shaft or elongated portion 358, and coupling portion 360. Coupling portion 360 may be used to engage closure member 106, shown in FIG. 7. Coupling portion 360 may engage tool portion 158 of closure member 106, shown in FIGS. 8-10. In some embodiments, driver 350 may include an inner shaft. The inner shaft may couple closure member 106 to driver 350. The inner shaft may couple to tool portion 158 of closure member 106 so that tool portion 158 is securely held after tool portion 158 is sheared off from closure member 106 during surgery. In some embodiments, an end of inner shaft may be press fit into tool portion 158. In some embodiments, the inner shaft may include a threaded end portion that engages a mating thread in tool portion 158. Rotation of the inner shaft may allow closure member 106 to be locked in coupling portion 360 of driver 350. Knob 362 may be used to rotate the inner shaft.

Reducer knob or dial 310 and reducer tube 313 work in concert to provide for reduction in a highly controlled manner. In some embodiments, turning reducer knob 310 clockwise about the central axis extends the height of reducer tube 313 and turning reducer knob 310 counterclockwise about the central axis retracts a portion of reducer tube 313 into reducer knob 310. Reducer tube 313 may have window 314 through which a portion of shaft 358 can be seen, as shown in FIG. 3. In some embodiments, the reducer tube may have more than one window. In some embodiments, connecting element 312 has one or more bumps or protruding features inside. In some embodiments, protruding feature(s) of connecting element 312 may pass through window(s) 314 of reducer tube 313 to engage and lock onto an extender sleeve (e.g., via recess 238 of extender 170 shown in FIG. 17). In some embodiments, the connecting element may have ridge(s), button(s) or other mechanism(s) that facilitate this engagement with the extender sleeve through the reducer tube.

In some embodiments, connecting element 312 can allow surgical personnel to adjust a distance between distractor handle 358 and common handle 330. For example, compressor handle 320 may have end 332 that is hollow inside to allow connecting element 312 moving in and out thereof, thereby changing the distance between distractor handle 358 and common handle 330. In some embodiments, connecting element 312 may have a corresponding end that can be removably attached to end 332. In some embodiments, connecting element 312 may have an outer portion that is affixed to end 332 and an inner portion that allows the reducer assembly (reducer knob 310 and reducer tube 313) to slide horizontally relative to common handle 330. Additional ways to provide adjustments for varying distances between reducer knob 310 and common handle 330 are described below.

In embodiments where connecting element 312 can be removably attached to end 332, connecting element 312 may have a quick connect mechanism that allows the reducer assembly, which in one embodiment comprises reducer knob 310 and reducer tube 313, to be switched out and connected to a different common handle, perhaps one without a compressor handle or one that is integrated with a compressor handle.

In some embodiments, common handle 330 may be pivotally coupled to connecting element 312 or compressor handle 320 at point 345. In embodiments disclosed herein, shaft 340 is fixedly attached to or made part of common handle 330 such that when moving common handle 330 in one direction, shaft 340 would pivot and move in an opposite direction. For example, for distraction, surgical personnel may squeeze common handle 330 and distractor handle 358 together or otherwise cause common handle 330 and reducer knob 310 to move toward each other, shaft 340 would move away from reducer tube 313 and hence the lower portion of shaft 358, if present, under reducer tube 313. As will be explained later, this motion would cause an increase in distance between extender sleeves which extend over shaft 340 and inside reducer tube 313. In embodiments where such extender sleeves are coupled to affected vertebral bodies via bone fastener assemblies, causing common handle 330 and reducer knob 310 to move toward each other would therefore cause the affected vertebral bodies to distract and pull away from each other. Examples of extender sleeves, bone fastener assemblies and ways to couple them to vertebral bodies are described in the above-referenced U.S. patent application Ser. No. 11/284,282 and U.S. Pat. No. 7,250,052, which are incorporated herein by reference as if set forth in full.

According to embodiments disclosed herein, the distance achieved by distraction can be locked using one or more locking mechanisms, thus holding the vertebral bodies in a distracted state during surgery. In some embodiments, surgical instrument 300 has one or more locking mechanisms for locking distractor handle 358 and common handle 330 of surgical instrument 300 and hence the distracted distance between vertebral bodies while allowing surgical personnel to perform a reduction using reducer knob 310 and reducer tube 313.

In some embodiments, surgical instrument 300 may further comprise compressor handle 320 coupled to connecting element 312 and common handle 330. In some embodiments, compressor handle 320 has an L-shape. For compression, surgical personnel may squeeze common handle 330 and compressor handle 330 together, moving them toward each other. This motion would have an opposite effect as the distraction described above. In this case, surgical personnel would cause the extender sleeves and hence the vertebral bodies coupled to the extender sleeves to move toward each other. According to some embodiments disclosed herein, this distance can also be locked via one or more locking mechanisms of surgical instrument 300.

Figure 4:
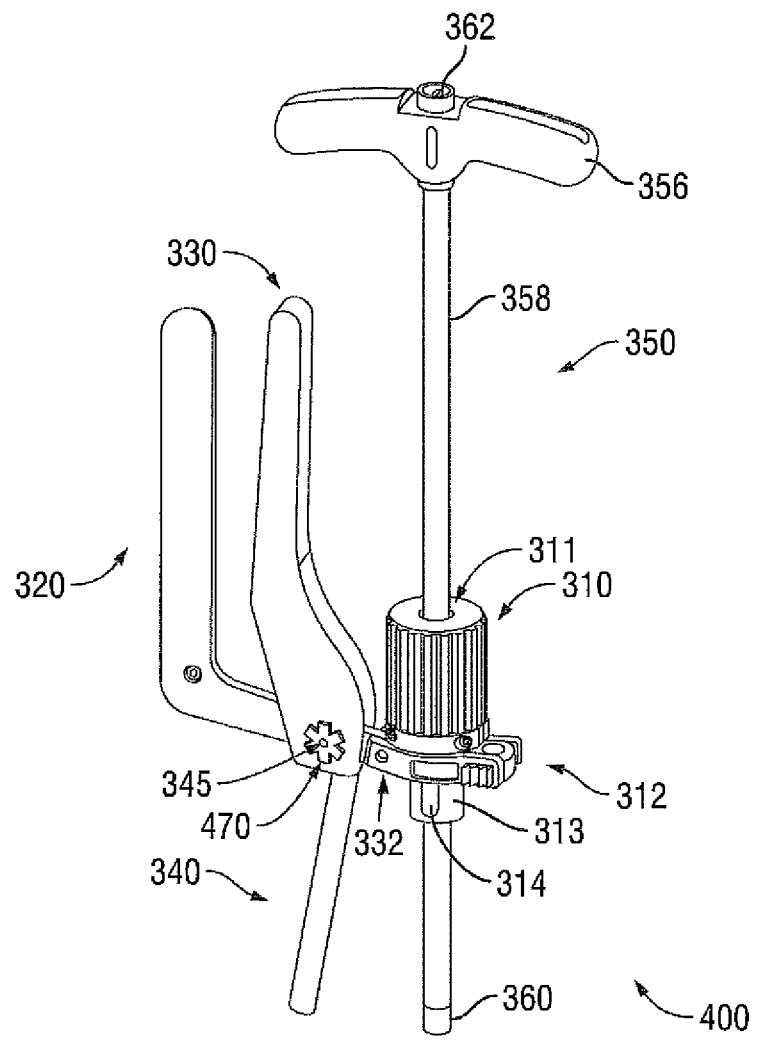
FIG. 4 depicts one embodiment of a surgical instrument with a distractor handle, a common handle, a compressor handle, and a locking mechanism for locking the common handle.

FIG. 4 depicts one embodiment of surgical instrument 400 with distractor handle 358, common handle 330, compressor handle 320, and locking mechanism 470 for locking common handle 330 at point 345. In one embodiment, common handle 330 pivots at point 345. In one embodiment, locking mechanism 470 is a pivot locking knob. In one embodiment, common handle 330 has an internal mechanism at point 345 working in concert with pivot locking knob 470 to allow surgical personnel to lock common handle 330 at various desired pivot angles. Other locking mechanisms are also possible. For example, in one embodiment, a locking pin or push button can take place of pivot locking knob 470. Correspondingly, common handle 330 may have an internal mechanism such as a spring or a catch at point 345.

In some embodiments, common handle 330 may have an internal spring mechanism that, at its equilibrium position, keeps common handle 330 oriented in an upright direction. Such a spring mechanism may exert forces that push when contracted or pull when extended, in proportion to the displacement of the spring from its equilibrium position. Thus, in some embodiments, a locking mechanism may utilize the elastic force or tension from the spring mechanism to lock common handle 330 and distractor handle 358 at a desired position, thus holding vertebral bodies coupled thereto at a certain distracted distance. For example, after moving common handle 330 towards distractor handle 358 and forcing the internal spring mechanism of common handle 330 to contract, surgical personnel may slide a fixed width bracket over common handle 330 and distractor 358. The elastic force or tension from the spring mechanism of common handle 330, in this case, would keep the bracket in place and thus the desired space between vertebral bodies. In this way, surgical personnel do not need to hold common handle 330 while performing a subsequent reduction.

In some embodiments, common handle 330 simply pivots at point 345 and relies on the elastic force or tension exerted by the affected vertebral bodies to keep the bracket in place.

In some embodiments, the surgical instrument may further comprise a surgical ratchet as a locking mechanism. In some embodiments, a ratchet arm is coupled to the common handle to ratchet with the distractor handle.

In some embodiments, the surgical instrument may further comprise a locking mechanism having a first portion, a second portion, and a lock. The first portion and the second portion of the locking means can be attached to the distractor handle and the common handle and locked using the lock.

Figure 5A:
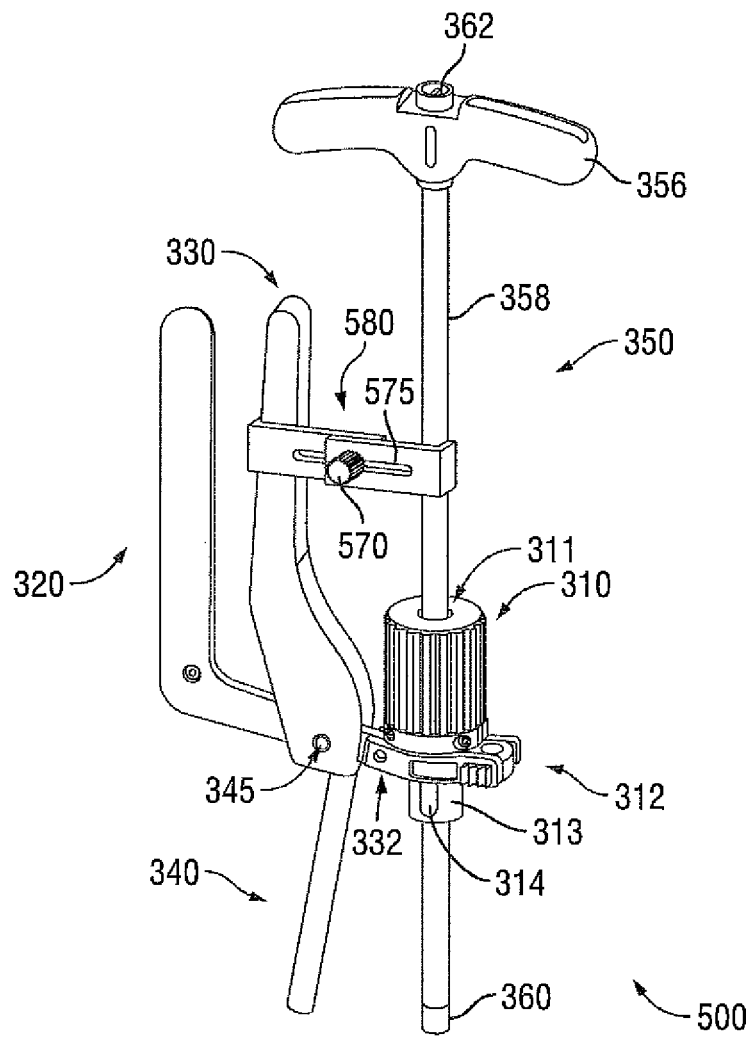
FIG. 5A depicts one embodiment of a surgical instrument with a distractor handle, a common handle, a compressor handle, and a locking mechanism for locking the common handle and the distractor handle.
Figure 5B:
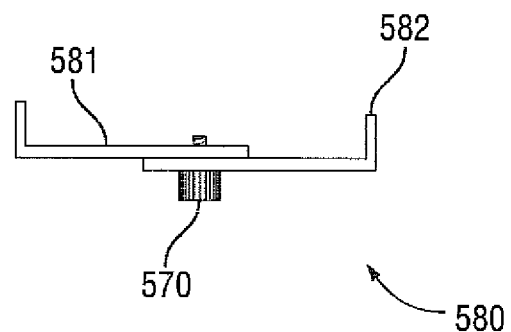
FIG. 5B depicts one embodiment of the locking mechanism of FIG. 5A.

FIG. 5A depicts one embodiment of surgical instrument 500 with distractor handle 358, common handle 330, compressor handle 320, and locking mechanism 580 for locking common handle 330 and distractor handle 358. FIG. 5B depicts a top view of locking mechanism 580. In the example of FIG. 5A and FIG. 5B, locking mechanism 580 comprises portions or arms 581 and 582, each of which has channel 575. Once arms 581 and 582 are coupled to common handle 330 and distractor handle 358 by tension as described above, lock 570 can slide along channel 575 and lock arms 581 and 582 at a fixed distance as determined by surgical personnel.

Figure 6:
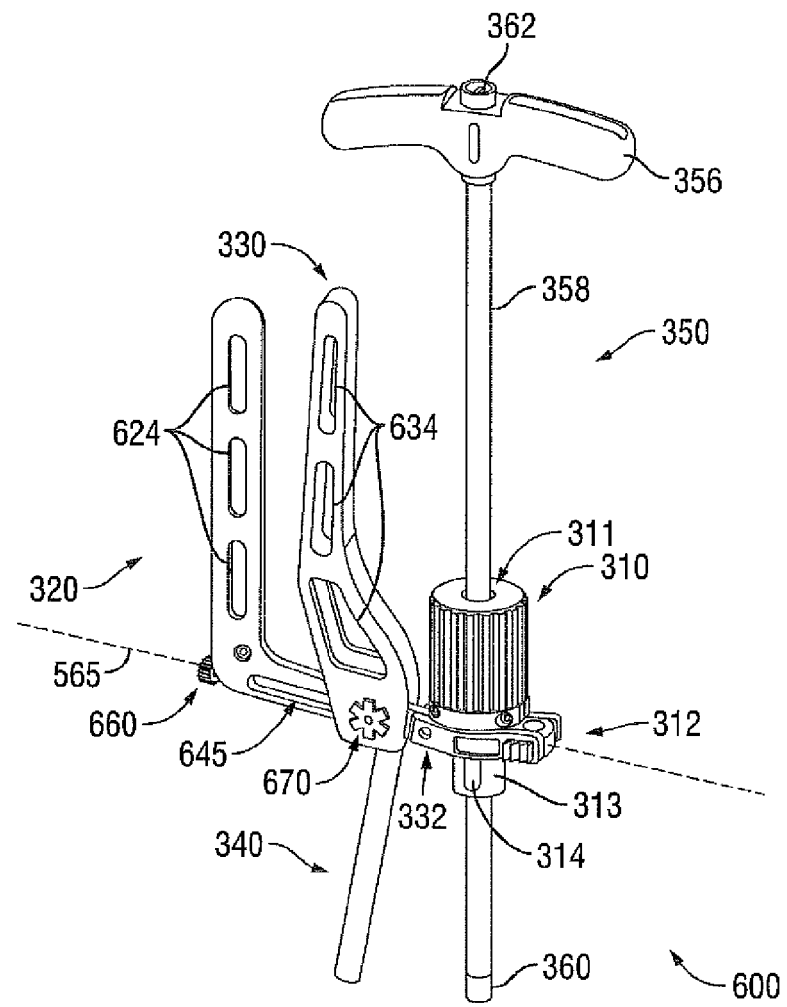
FIG. 6 depicts one embodiment of a surgical instrument with a distractor handle, a common handle, a compressor handle, an adjusting means for adjusting the distance between the common handle and the compressor handle and a locking mechanism for locking the common handle at the desired distance and angle.

FIG. 6 depicts one embodiment of surgical instrument 600 with distractor handle 358, common handle 330, compressor handle 320, adjusting means 660 for adjusting the distance between common handle 330 and compressor handle 320, and locking mechanism 670 for locking common handle 330 at a desired distance and angle. In some embodiments, adjusting means 660 comprises a dial coupled to compressor handle 320 and an inner shaft coupled to the dial and common handle 330. In some embodiments, locking mechanism 670 comprises a pivot locking knob coupled to common handle 330 via channel 645 having central axis 565. In some embodiments, turning dial 660 moves common handle 330 away from or towards compressor handle 320 along channel 645 and adjusts a distance between compressor handle 320 and common handle 330 relative to central axis 565. In some embodiments, locking pivot locking knob 670 locks the distance between compressor handle 320 and common handle 330. Other ways to adjust the distance between compressor handle 320 and common handle 330 are also possible. For example, adjusting means 660 may comprise an adjustable rack coupled to common handle 330.

Some embodiments of a surgical instrument disclosed herein may have various features to reduce the weight, making it easier to handle. In some embodiments, compressor handle 320 of surgical instrument 600 may have one or more weight reducing windows 624. In some embodiments, common handle 330 of surgical instrument 600 may have one or more weight reducing windows 634. As one skilled in the art can appreciate, weight reducing windows, holes, cavities, recesses, and the like may be implemented at various non-structural portions of the surgical instrument disclosed herein. In some cases, a window may be made for other purposes. For example, in one embodiment, a portion of the inner shaft may be implemented as a gauge. Channel 645 may be implemented to show the gauge. Corresponding measurements may be marked near channel 645 on compressor handle 320 along axis 565. In this way, surgical personnel can use the gauge and precisely adjust the distance between compressor handle 320 and common handle 330 and hence the distance between common handle 330 and distractor handle 358.

In embodiments disclosed herein, various locking mechanisms as well as adjusting mechanisms of the surgical instrument can provide a gradual lockable change in distance between the affected vertebral bodies, allowing surgical personnel to then focus on performing a reduction, perhaps to correct a spondylolisthesis. As discussed above, often during a spondylolisthesis, one vertebra overlaps another. That is, the lower vertebra gets caught under the hard cortical posterior rim of the upper vertebra, thus impeding any movement to correct the condition. Embodiments of a surgical instrument disclosed herein incorporate mechanisms for compression, distraction, and reduction and provide a single instrument to perform maneuvers typically done by multiple instruments in a spinal stabilization procedure. Examples of a spinal stabilization procedure are described in the above-referenced U.S. patent application Ser. No. 11/284,282 and U.S. Pat. No. 7,250,052, which are incorporated herein by reference as if set forth in full.

Figure 7:
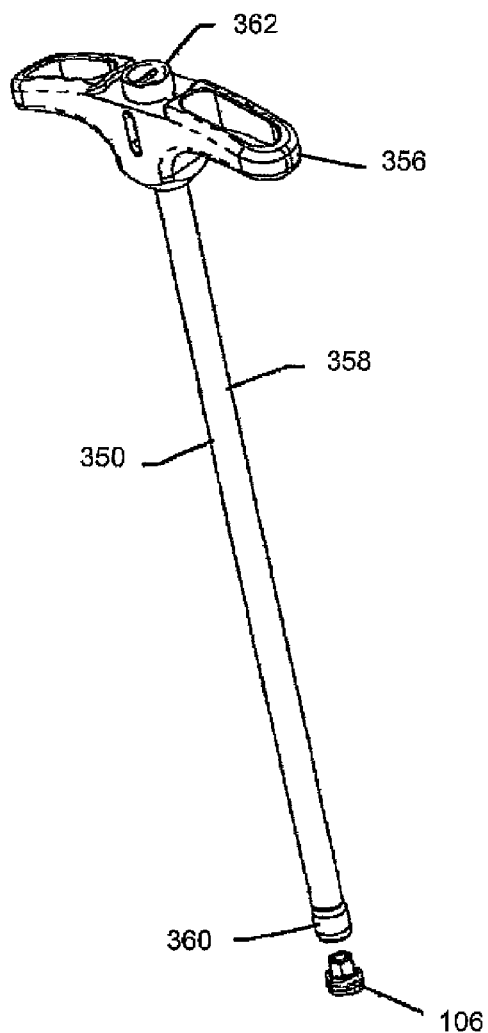
FIG. 7 depicts one embodiment of a driver utilized as a distractor handle.

FIG. 7 depicts one embodiment of driver 350 which may be used in a spinal stabilization procedure to position a closure member in a collar of a bone fastener assembly. As shown in FIG. 7, driver 350 may include handle 356, elongated portion 358, and coupling portion 360. In some embodiments, elongated portion 358 can be utilized as a distractor handle. Coupling portion 360 may be used to engage closure member 106. Coupling portion 360 may engage tool portion 158 of closure member 106, shown in FIGS. 8-10. In some embodiments, driver 350 may include an inner shaft. The inner shaft may couple closure member 106 to driver 350. The inner shaft of driver 350 may couple to tool portion 158 of closure member 106 so that tool portion 158 is securely held after tool portion 158 is sheared from closure member 106 during surgery. In some embodiments, an end of inner shaft may be press fit into tool portion 158. In some embodiments, the inner shaft may include a threaded end portion that engages a mating thread in tool portion 158. Rotation of the inner shaft may allow closure member 106 to be locked in coupling portion 360 of driver 350. Knob 362 may be used to rotate the inner shaft.

Figure 8:
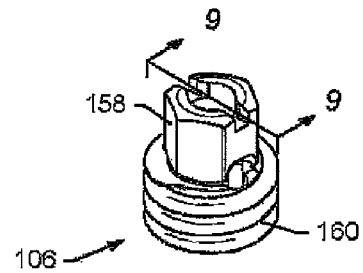
FIG. 8 depicts a perspective view of a closure member for a bone fastener assembly.

FIG. 8 depicts a perspective view of closure member 106 for a bone fastener assembly. Closure member 106 may include tool portion 158 and mate threading 160. Tool portion 158 may couple to a tool that allows closure member 106 to be positioned in a collar of a bone fastener assembly. Tool portion 158 may include various configurations (e.g., threads, hexalobular connections, hexes) for engaging a tool (e.g., a driver). Male threading 160 may have a shape that complements the shape of female threading in arms of a collar.

Figure 9:
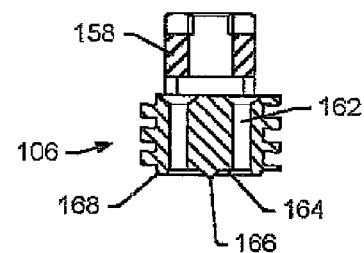
FIG. 9 depicts a cross-sectional representation of the closure member taken substantially along plane 9-9 indicated in FIG. 8.

FIG. 9 depicts a cross-sectional representation of closure member 106 taken substantially along plane 9-9 of FIG. 8. Closure member 106 may include removal openings 162. A drive tool may be inserted into removal openings 162 to allow removal of closure member 106 after tool portion 158 has been sheared off. Removal openings 162 may include any of a variety of features including, but not limited to, sockets, holes, slots, and/or combinations thereof. In an embodiment, removal openings 162 are holes that pass through bottom surface 164 of closure member 106.

A bottom surface of a closure member may include structure and/or texturing that promotes contact between the closure member and an elongated member. A portion of the structure and/or texturing may enter and/or deform an elongated member when the closure member is coupled to the elongated member. Having a portion of the closure member enter and/or deform the elongated member may couple the elongated member to the closure member and a bone fastener assembly so that movement of the elongated member relative to the bone fastener assembly is inhibited. In a closure member embodiment, such as the embodiment depicted in FIG. 9, bottom surface 164 of closure member 106 may include point 166 and rim 168. In some embodiments, rim 168 may come to a sharp point. In some embodiments, a height of rim 168 may be less than a height of point 166. In other embodiments, a height of rim 168 may be the same or larger than a height of point 166. In some embodiments, rim 168 may not extend completely around the closure member. For example, eight or more portions of rim 168 may be equally spaced circumferentially around closure member 106. In certain embodiments, a solid central core including point 166 and rim 168 may enhance the ability of closure member 106 to secure an elongated member in a collar.

Figure 10:
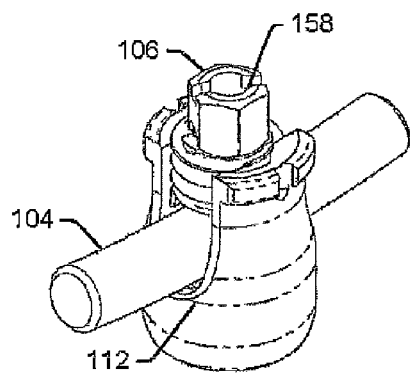
FIG. 10 depicts a perspective view of a portion of a spinal stabilization system having the closure member of FIG. 8 resting on top of a rod which is seated in a collar of a bone fastener assembly.

FIG. 10 depicts a perspective view of a portion of a spinal stabilization system having closure member 106 of FIG. 8 resting on top of rod 104 which is seated in collar 112 of a bone fastener assembly. Closure member 106 may couple to collar 112 by a variety of systems including, but not limited to, standard threads, modified threads, reverse angle threads, buttress threads, or helical flanges. Closure member 106 may be advanced into an opening in a collar to engage a portion of elongated member 104. In some embodiments, closure member 106 may inhibit movement of elongated member 104 relative to collar 112.

Figure 11:
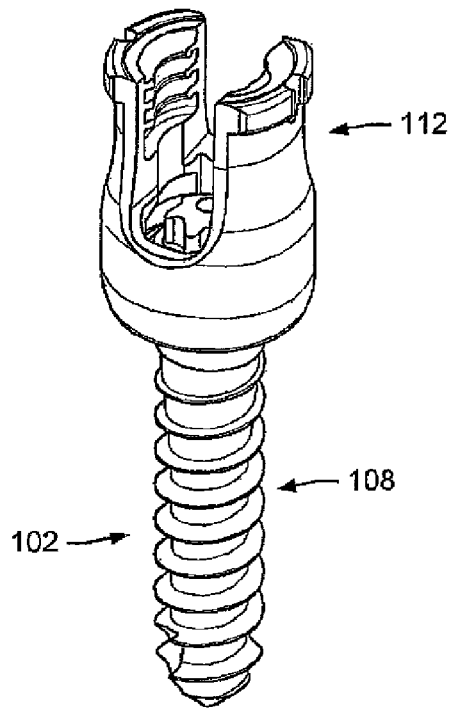
FIG. 11 depicts a perspective view of an embodiment of a bone fastener assembly.
Figure 12:
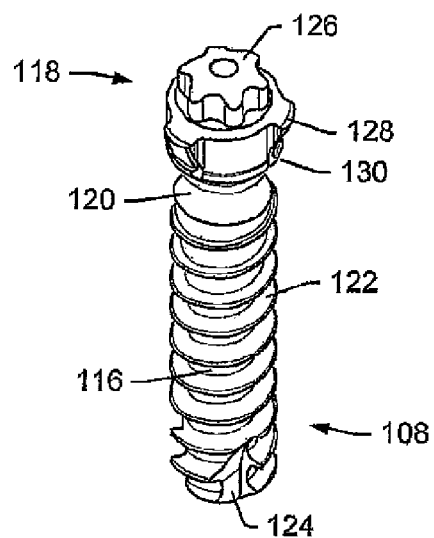
FIG. 12 depicts a perspective view of an embodiment of a bone fastener for the bone fastener assembly of FIG. 11.
Figure 13:
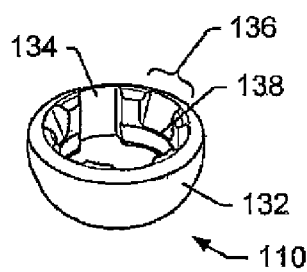
FIG. 13 depicts a perspective view of an embodiment of a ring for the bone fastener assembly of FIG. 11.
Figure 14:
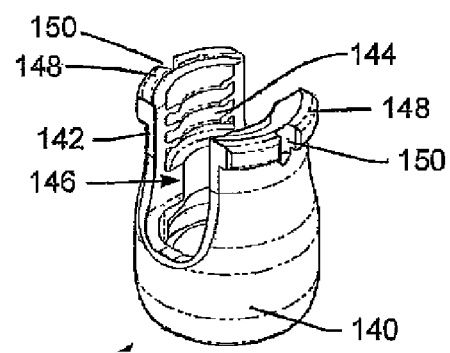
FIG. 14 depicts a perspective view of an embodiment of a collar for the bone fastener assembly of FIG. 11.

FIG. 11 depicts a perspective view of an embodiment of bone fastener assembly 102. FIGS. 12-14 depict embodiments of bone fastener assembly components. Components of bone fastener assembly 102 may include, but are not limited to, bone fastener 108 (shown in FIG. 12), ring 110 (shown in FIG. 13), and collar 112 (shown in FIG. 14). Bone fastener 108 may couple bone fastener assembly 102 to a vertebra. Ring 110 may be positioned between a head of bone fastener 108 and collar 112.

FIG. 12 depicts an embodiment of bone fastener 108. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone. Head 118 of bone fastener 108 may include various configurations to engage a driver that inserts the bone fastener into a vertebra. In some embodiments, the driver may also be used to remove an installed bone fastener from a vertebra. In some embodiments, head 118 may include one or more tool portions 126. Tool portions 126 may be recesses and/or protrusions designed to engage a portion of the driver. Head 118 of bone fastener 108 may include one or more splines 128, as depicted in FIG. 12. In some head embodiments, head 118 may include three splines. Splines 128 may be equally spaced circumferentially around head 118 of bone fastener 108. In some head embodiments, splines 128 may be spaced at unequal distances circumferentially around head 118. Splines 128 may include various surface configurations and/or texturing to enhance coupling of bone fastener 108 with a ring of a bone fastener assembly. In some embodiments, sides of the splines may be tapered so that the splines form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, the splines may include recessed surfaces that accept projections extending from surfaces of the ring.

Neck 120 of bone fastener 108 may have a smaller diameter than adjacent portions of head 118 and shank 116. The diameter of neck 120 may fix the maximum angle that the collar of the bone fastener assembly can be rotated relative to bone fastener 108. In some embodiments, neck 120 may be sized to allow up to about 40 degree or more of angulation of the collar relative to the bone fastener. In some embodiments, the neck may be sized to allow up to about 30 degree of angulation of the collar relative to the bone fastener. In some embodiments, the neck may be sized to allow up to about 20 degree of angulation of the collar relative to the bone fastener.

FIG. 13 depicts a perspective view of an embodiment of ring 110. Outer surface 132 of ring 110 may have a contour that substantially complements a contour of an inner surface of a collar in which the ring resides. A contour of the outer surface of the ring may be a spherical portion. When the ring is positioned in the collar, the complementary shape of the ring outer surface and the inner surface of the collar that contacts the ring allows angulation of the collar relative to a bone fastener coupled to the ring. The contour of the outer surface of the ring and the inner surface of the collar may inhibit removal of the ring from the collar after insertion of the ring into the collar. Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of the outer surface of the ring. An inner surface of ring 110 may include one or more grooves 134 and/or one or more seats 136. Seats 136 may be circumferentially offset from grooves 134. Grooves 134 may be sized to allow passage of splines 128 of bone fastener 128 through ring 110. When splines 128 are inserted through grooves 134, bone fastener 108 may be rotated until splines 128 align with seats 136. Bone fastener 108 may be pulled or driven so that splines 128 are positioned in seats 136. In some embodiments, projections 130 may pass over ridges 138 of ring 110. Passage of projections 130 over ridges 138 may securely couple bone fastener 108 to ring 110 and inhibit separation of ring 110 from bone fastener 108.

As used herein, the term "collar" includes any element that wholly or partially encloses or receives one or more other elements. A collar may enclose or receive elements including, but not limited to, a bone fastener, a closure member, a ring, and/or an elongated member. In some embodiments, a collar may couple two or more other elements together (e.g., an elongated member and a bone fastener). In some embodiments, a collar may have a "U" shape, however it is to be understood that a collar may also have other shapes.

FIG. 14 depicts a perspective view of an embodiment of collar 112 for bone fastener assembly 102. Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow an extender to be coupled to arms 142 without substantially increasing a maximum effective outer diameter along a length of collar 112. Thus, a reduced width across arms 142 may reduce bulk at a surgical site.

Inner surfaces of arms 142 may include threading 144. Threading 144 may engage complementary threading of a closure member (e.g., closure member 106) to secure an elongated member (e.g., rod 104) to a bone fastener assembly (e.g., bone fastener assembly 102). Arms 142 and body 140 may form slot 146. Slot 146 may be sized to receive an elongated member. When an elongated member is positioned in slot 146, a portion of the elongated member may contact a head of a bone fastener positioned in the collar. Arms 142 may include ridges or flanges 148. Flange 148 may allow collar 112 to be coupled to an extender so that translational motion of the collar relative to the extender is inhibited. Flanges 148 may also include notches 150. A movable member of an extender may extend into notch 150. When the movable member is positioned in notch 150, a channel in the extender may align with a slot in collar 112. With the movable member positioned in notch 150, rotational movement of collar 112 relative to the extender may be inhibited.

A bone fastener may be positioned in a collar such that the bone fastener is able to move radially and/or rotationally relative to the collar (or the collar relative to the bone fastener) within a defined range of motion. Motion of the bone fastener relative to the collar (or the collar relative to the bone fastener) may be referred to as "angulation" and/or "polyaxial movement". A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments.

Various instruments may be used in a minimally invasive procedure to form a spinal stabilization system in a patient. The instruments may include, but are not limited to, positioning needles, guide wires, dilators, bone awls, bone taps, sleeves, extenders, drivers, tissue wedges, elongated member length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and closure members.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may be, or may include, components that cannot be autoclaved or chemically sterilized. Instruments or components of instruments that cannot be autoclaved or chemically sterilized may be made of sterile materials.

An extender, sometimes referred to herein as an extender sleeve, may be used as a guide to install a bone fastener of a bone fastener assembly in a vertebra. An extender may be coupled to a-collar of a bone fastener assembly. A distal end of an extender may be tapered or angled to reduce bulk at a surgical site. Instruments may be inserted into the extender to manipulate the bone fastener assembly. Movement of the extender may alter an orientation of a collar relative to a bone fastener of the bone fastener assembly. In some embodiments, an extender may be used as a retractor during a spinal stabilization procedure. In some embodiments, an extender may include a quick connect mechanism that allows the extender to quickly and securely couple to a collar of a bone fastener assembly. Such an extender may also include a quick release mechanism to allow the extender to be quickly removed and detached from the collar of the bone fastener assembly.

An extender for a single-level vertebral stabilization system may include one or more channels in a wall of the extender to allow access to an adjacent vertebra. For some single-level vertebral stabilization procedures, only single-channel extenders (i.e., extenders with a single channel in a wall of the extender) may be used. For other single-level vertebral stabilization procedures, one or more multi-channel extenders (i.e., extenders with two or more channels in a wall of the extender) may be used. Channels may provide flexibility to or enhance flexibility of a multi-channel extender. In some embodiments, a proximal portion of a multi-channel extender may have a solid circumference. A region of solid circumference in a multi-channel extender may enhance stability of the multi-channel extender. In some embodiments, a multi-channel extender may be longer than a single-channel extender.

Instruments may access a bone fastener assembly through a passage in an extender. In some embodiments, a channel in a wall of an extender may extend a full length of the extender. In some embodiments, especially in embodiments of multi-channel extenders, a channel in a wall of an extender may extend only a portion of the length of the extender. A channel may extend to a distal end of an extender such that an elongated member inserted in the channel may pass from the extender into a slot of a collar of a bone fastener assembly coupled to the extender. A channel in an extender may be any of a variety of shapes. A channel may have a width that exceeds a width (e.g., a diameter) of an elongated member that is to be inserted in the channel. In some embodiments, a channel may be a linear opening parallel to a longitudinal axis of the extender.

Movable members may extend through portions of an extender proximate a channel in the extender. Movable members may engage notches in a collar to establish a radial orientation of the extender on the collar and/or to inhibit rotation of the collar relative to the extender. In some embodiments, a distal end of a movable member may be a projection that engages an opening in a collar. In certain embodiments, a proximal end of a movable member may include a tool portion. The tool portion may facilitate engaging the collar with the extender.

Figure 15:
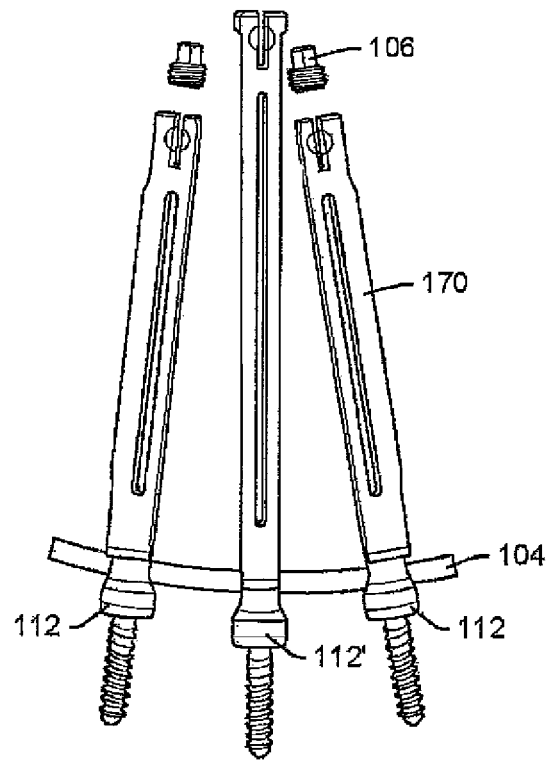
FIG. 15 depicts one embodiment of a spinal stabilization system before reduction.

FIG. 15 depicts one embodiment of a spinal stabilization system used in a multi-level stabilization procedure. An extender used at a middle vertebra in a multi-level stabilization procedure may be a multi-channel extender. Channels in a multi-channel extender may allow access to adjacent vertebrae from a middle vertebra. An extender used at an end vertebra of a multi-level stabilization system may be a single-channel extender or a multi-channel extender. A system for coupling a bone fastener assembly to a multi-channel extender may include a limiter that inhibits spreading of arms of the extender to inhibit release of the bone fastener assembly from the extender.

Figure 16:
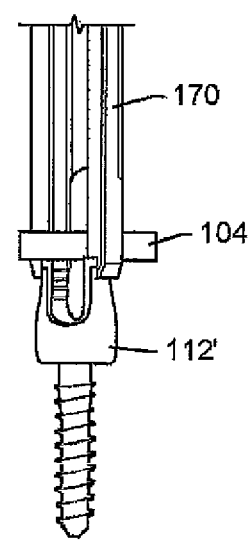
FIG. 16 depicts one embodiment of an unseated elongated member before reduction.

During some spinal procedures, the elongated member may not initially seat in collars of the bone fastener assemblies. During such procedures, a reducer may be used to seat the elongated member in the collars of the bone fastener assemblies. As shown in FIG. 15, before reduction is initiated, elongated member 104 may be positioned in collars 112 coupled to extenders 170 as depicted in FIG. 15. Closure members 106 may be positioned in one or more collars 112 and 112' such that elongated member 104 is at least loosely positioned in one or more of the collars. In the example of FIG. 15, elongated member 104 may be fully seated in collars 112 and not be fully seated in collar 112'. FIG. 16 depicts an enlarged perspective view of elongated member 104 proximate collar 112'.

In some cases, reduction may be performed to correct a deformity in a patients spine. For a multi-level spinal stabilization system, reduction may facilitate seating of an elongated member in a collar of the spinal stabilization system. Embodiments of the surgical instrument disclosed herein may be used with a spinal stabilization system to allow a final position of a spine to be manipulated according to the contour of the elongated member.

Figure 17:
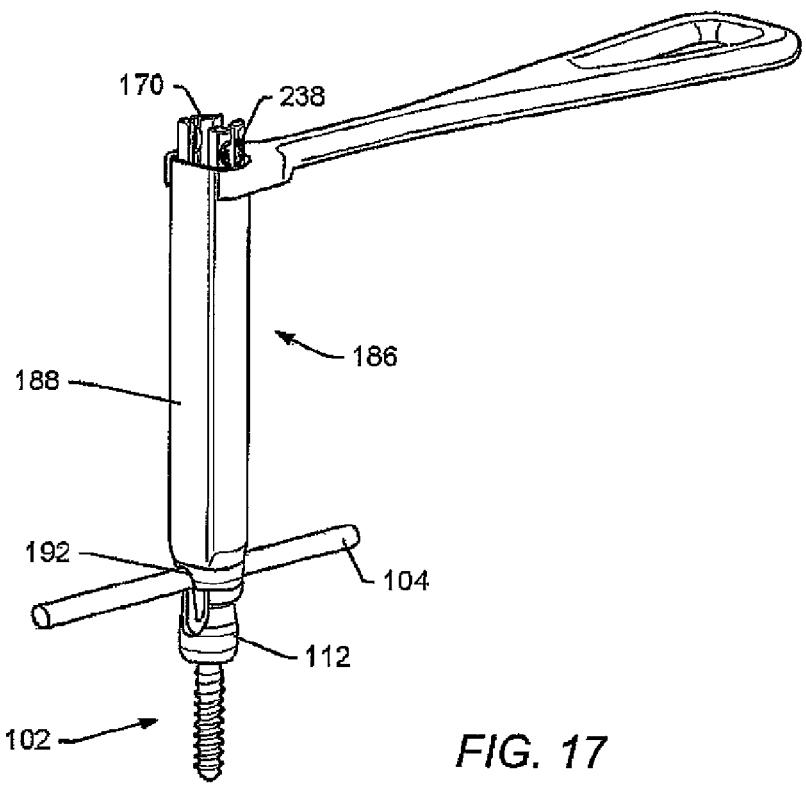
FIG. 17 depicts a perspective view of one embodiment of a counter torque assembly coupled to a bone fastener assembly via an extender sleeve.

In some embodiments, the surgical instrument disclosed herein may be used in combination with a sleeve or tube to forcefully reduce the difference in anterior-posterior position of one vertebral body with respect to one or more adjacent vertebral bodies coupled to a spinal stabilization system. FIG. 17 depicts a perspective view of one embodiment of a counter torque assembly having tube 186 positioned over extender sleeve 170 coupled to collar 112 of bone fastener assembly 102 and engaging elongated member or rod 104 in groove or cutout 192. In a multi-level spinal stabilization system, elongated member or rod 104 may be fixed in place at one or more positions (e.g., secured in one or more of the outer collars with a closure member). A length of hollow shaft 188 of tube 186 may be chosen such that a proximal end of extender 170 protrudes from the proximal opening of tube 186. In some embodiments, an instrumentation kit may provide tubes 186 and extenders 170 that are sized to be used together such that recesses 238 in a proximal end of extender 170 are exposed above tube 186 during use.

Figure 18:
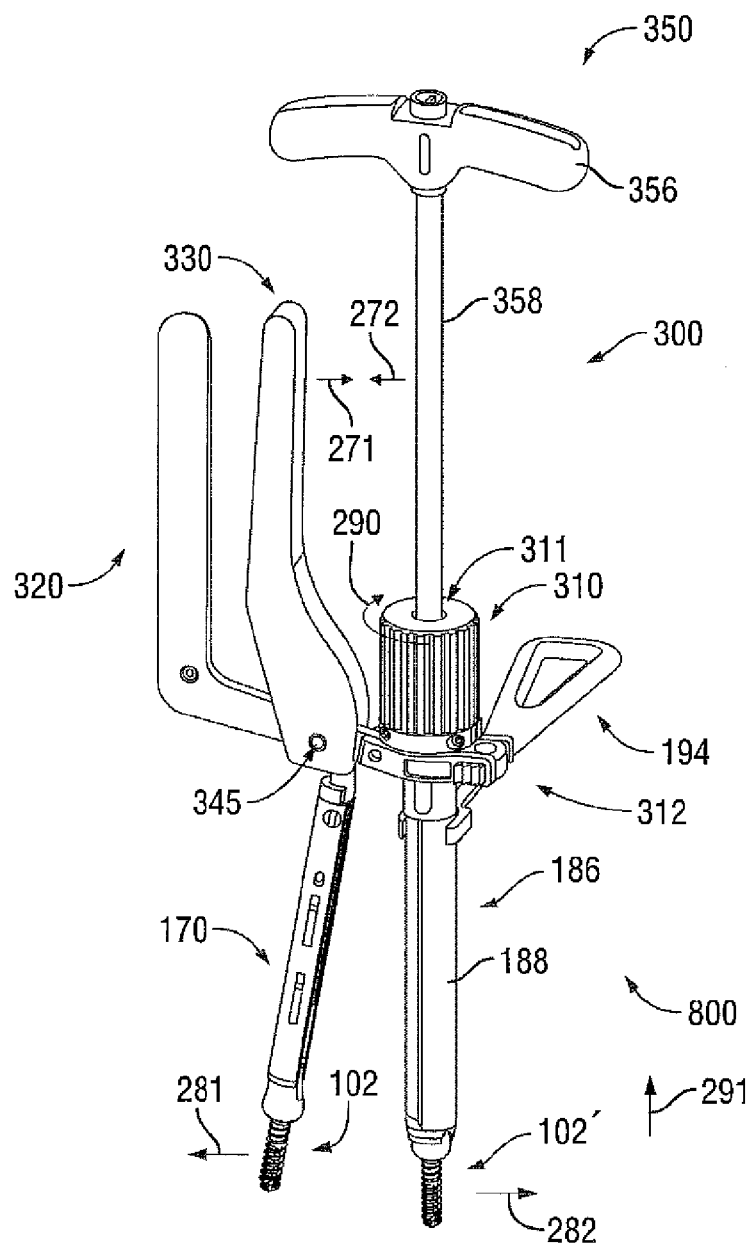
FIG. 18 depicts a perspective view of one embodiment of a surgical instrument in use with a counter torque assembly.

FIG. 18 depicts a perspective view of one embodiment of surgical instrument 300 in use with counter torque assembly 800. In one embodiment, counter torque assembly 800 comprises counter torque handle 194 and tube 186 having shaft 188. In one embodiment, interior of reducer tube 313 may have protruding features that complement recesses 238 in the proximal end of extender 170 exposed above tube 186 as described above. In one embodiment, such protruding features inside reducer tube 313 may allow reducer tube 313 to slide over extender sleeve 170 and engage extender sleeve 170 with a click. In some embodiments, connecting element 312 has protruding features inside to further engage and lock onto recesses 238. In some embodiments, an instrumentation kit may provide tubes 186 and extenders 170 that are sized to be used together such that when reducer tube 313 clicks onto the proximal end of extender 170 exposed above tube 186 reducer tube 313 would touch or substantially near tube 186 of counter torque assembly 800. In this way, surgical instrument 300 can be quickly and slidably coupled to bone fastener assembly 102' by way of extender sleeve 170 and tube 186 is positioned under reducer tube 313 of surgical instrument 300 and over extender sleeve 170. In one embodiment, bone fastener assembly 102 is anchored at an end vertebra and shaft 340 is coupled to bone fastener assembly 102 by way of extender sleeve 170. In one embodiment, bone fastener assembly 102' is anchored at a middle vertebra in a multi-level stabilization procedure. In one embodiment, bone fastener assembly 102' is anchored at an end vertebra in a single level stabilization procedure.

As described above, in some embodiments, surgical instrument 300 may comprise reducer knob 310, connecting element 312, common handle 330, and compressor handle 320. Reducer knob 310 may have first passage 311 through which shaft 358 of driver 350 is acceptable. Connecting element 312 may be coupled to reducer knob 310 and having a second passage through which shaft 358 of driver 350 is acceptable. Compressor handle 320 may be coupled to common handle 330 via connecting element 312. Common handle 330 may pivot at point 345, between reducer knob 310 and compressor handle 320. In some embodiments, a portion of compressor handle 320 is vertically oriented and perpendicular to connecting element 312. In some embodiments, compressor handle 320 has an L-shape.

In some embodiments, a surgical method may comprise moving common handle 330 of surgical instrument 330 towards distractor handle 358 in a first direction as indicated by arrow 271. Optionally, in one embodiment, distractor handle 358 may also be moved towards common handle 330 in a second direction as indicated by arrow 272. As depicted in FIG. 18, moving common handle 330 in first direction 271 causes the lower portion of common handle 330 (i.e., shaft 340) and hence extender sleeve 170 coupled thereto to move in the opposite direction as indicated by arrow 281. Similarly, moving common handle 330 and distractor handle 358 in directions 271 and 272 cause extenders 170 to move in opposite directions 281 and 282, thereby increasing the distance between vertebral bodies that anchor bone fastener assemblies 102 and 102'.

In some embodiments, the distracted distance between vertebral bodies can be locked using one or more locking mechanisms of surgical instrument 300 as described above. Thus, in some embodiments, the surgical method may further comprise locking common handle 330 and distractor handle 358 to hold the distracted distance between vertebral bodies that anchor bone fastener assemblies 102 and 102'.

Figure 19:
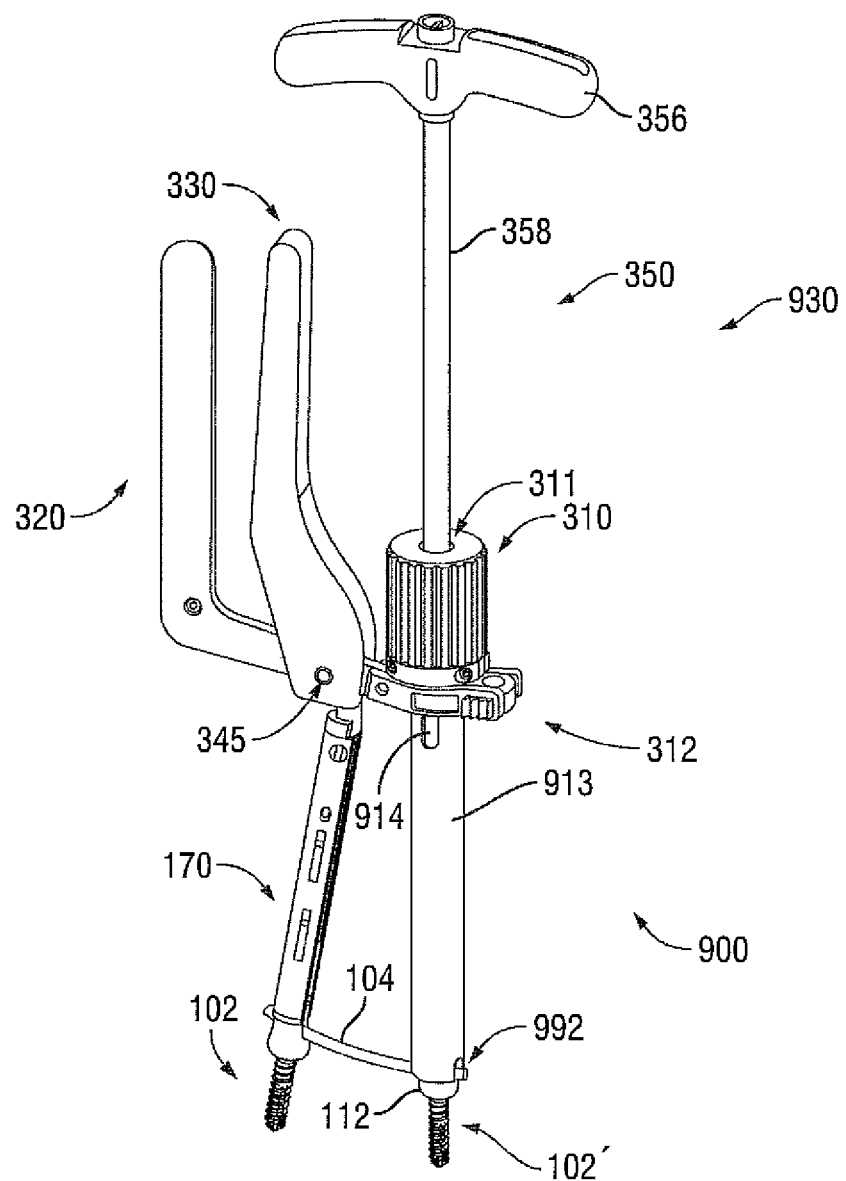
FIG. 19 depicts a perspective view of one embodiment of a surgical instrument coupled to a portion of one embodiment of a spinal stabilization system.

In some embodiments, the surgical method may further comprise performing a reduction while surgical instrument 300 holds the affected vertebrae in a distracted state. In some embodiments, surgical personnel may turn reducer knob 310 to adjust a height of reducer tube 313 as discussed above. One end of reducer knob 310 may have an inner diameter sufficiently large to accommodate an outer diameter of reducer tube 313 such that a portion of reducer tube 313 may be retracted into reducer knob 310. In one embodiment, to perform a reduction, surgical personnel may turn reducer knob 310 of surgical instrument 300 (e.g., in a direction as indicated by arrow 290) to extend a portion of reducer tube 313 out from reducer knob 310 to contact and/or further press against tube 186 of counter torque assembly 800. In some embodiments, reducer tube 313 may have a non-threaded end for engaging counter torque tube 186. As reducer tube 313 pushes tube 186 to go down and hit rod 104 as shown in FIG. 19, coupling portion 360 of driver 350 may engage closure member 106 of bone fastener assembly 102 as described above with reference to FIGS. 7-10. As described above, the inner shaft of driver 350 can be securely coupled to tool portion 158 of closure member 106 (e.g., in some embodiments, the inner shaft may include a threaded end portion that engages a mating thread in tool portion 158 and rotation of the inner shaft may allow closure member 106 to be locked in coupling portion 360 of driver 350). As reducer tube 313 pushes tube 186 to go down, the inner shaft of driver 350 remains coupled to tool portion 158 of closure member 106. At this point, closure member 106 may not be connected to bone fastener assembly 102'. Much of the time, the closure top (e.g., closure member 106) just sits in the extender sleeve on top of the rod (e.g., rod 104) until the vertebra is reduced and the closure top can come in contact with the collar threads to begin threading (e.g., male threading 160 of closure member 106 may begin threading with inner threading 144 of arms 142 of collar 112). In the mean time, the connection of connecting element 312 to recesses 238 of extender 170 (e.g., via interior protruding features of connecting element 312 through window(s) 314 of reducer tube 313) pulls bone fastener assembly 102' upwards in a direction as indicated by arrow 291. In this way, a vertebra anchoring bone fastener assembly 102' can be gradually pulled up into alignment with adjacent vertebrae as reducer tube 313 holds rod 104 down. In embodiments described above with reference to FIG. 18, the reducer tube does not extend over the entire extender sleeve. Instead, the reducer tube pushes against a counter torque tube which, in turn, pushes against a rod and holds it down as the bone fastener, along with the vertebra that anchors it, is being pulled up.

FIG. 19 depicts a perspective view of one embodiment of surgical instrument 900 in use with spinal stabilization system 930. Similar to surgical instrument 300 described above, surgical instrument 900 comprises integrated mechanisms for distraction, reduction, and compression. In one embodiment, surgical instrument comprises distractor handle 358, reducer knob 310, reducer tube 913, common handle 330, and compressor handle 320. Distractor handle 358 can be a part of driver 350 and may couple to bone fastener assembly 102' through passage 311 and extender sleeve 170 as described above. Reducer tube 913 is coupled to reducer knob 310 via connecting element 312, is of sufficient size to accept and extend over extender sleeve 170, and has cutouts 992 to straddle elongated member 104. In some embodiments, window 914 of reducer tube 913 may allow surgical personnel to inspect whether surgical instrument 900 properly engages extender sleeve 170.

In some embodiments, reducer tube 913 extends over the entire extender sleeve 170. Thus, as surgical personnel turn reducer knob 310 clockwise, reducer tube 913 extends downwards and begins to straddle and/or push against elongated member 104 via cutouts 992. As reducer tube 913 pushes down on elongated member 104, the connection of connecting element 312 to recess 238 of extender 170 via window(s) 914 of reducer tube 913 pulls bone fastener assembly 102' upwards in a direction as indicated by arrow 291. In this way, elongated member 104 can be properly seated in collar 112 of bone fastener assembly 102' and a vertebra anchoring bone fastener assembly 102' can be gradually pulled up into alignment with adjacent vertebrae.

Figure 20:
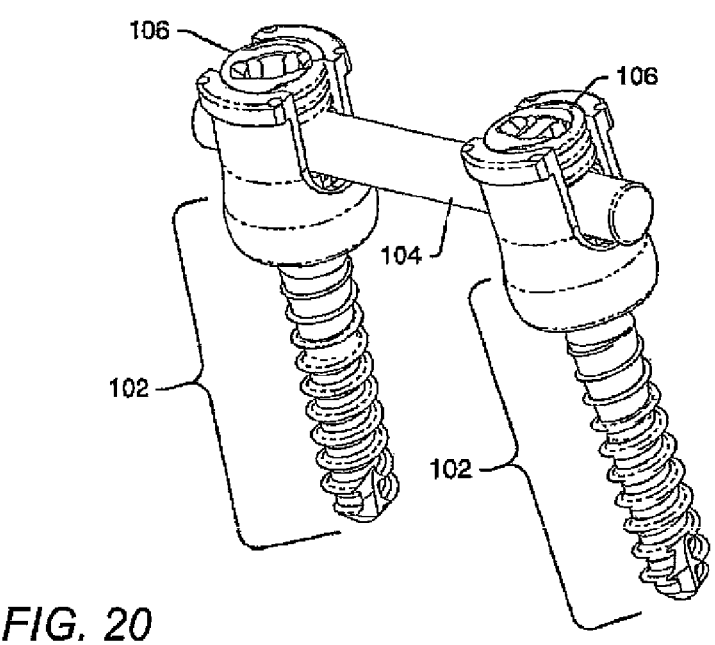
FIG. 20 depicts a perspective view of a portion of one embodiment of a spinal stabilization system after reduction in which an elongated member is properly seated in collars of bone fastener assemblies.

FIG. 20 depicts a perspective view of one embodiment of a spinal stabilization system after reduction in which elongated member 104 is properly seated in collars of bone fastener assemblies 102 and tool portion 158 is sheared off from closure member 106. FIG. 20 depicts a spinal stabilization system for one vertebral level. In some embodiments, the spinal stabilization system of FIG. 20 may be used as a multi-level spinal stabilization system if one or more vertebrae are located between the vertebrae in which bone fastener assemblies 102 are placed. In other embodiments, multi-level spinal stabilization systems may include additional bone fastener assemblies to couple to one or more other vertebrae.

Embodiments of a surgical instrument useful for reducing spondylolisthesis have now been described in detail. Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as examples of embodiments. Elements and materials may be substituted for or implemented from those illustrated and described herein, as would be apparent to one skilled in the art after having the benefit of the disclosure. Changes may be made in the elements or to the features described herein without departing from the spirit and scope of the disclosure as set forth in the following claims and their legal equivalents.

What is claimed is:

1. A surgical instrument with integrated mechanisms for distraction, compression, and reduction of vertebrae, comprising:
 a reducer knob having an aperture extending therethrough;
 a reducer tube coupled to said reducer knob;

a connecting element coupled to said reducer knob and said reducer tube, wherein said reducer knob aperture, said connecting element, and said reducer tube have an inner diameter that accommodates a distractor handle, wherein the reducer knob, reducer tube and connecting element are longitudinally aligned;

a common handle pivotally coupled to said connecting element;

a compressor handle coupled to said connecting element and said common handle; and a shaft fixedly attached to or made part of said common handle, wherein moving said common handle towards said distractor handle increases a distance between said shaft and said reducer tube, wherein moving said common handle towards said compressor handle decreases said distance between said shaft and said reducer tube, wherein turning said reducer knob in a first direction extends a height of said reducer tube, and wherein turning said reducer knob in a second direction retracts a portion of said reducer tube into said reducer knob.

2. The surgical instrument of claim 1, wherein said compressor handle is coupled to said connecting element and said common handle such that the common handle is disposed between said compressor handle and said reducer knob.

3. The surgical instrument of claim 1, wherein said compressor handle has an L-shape.

4. The surgical instrument of claim 2, further comprising a dial coupled to said compressor handle and a pivot locking knob coupled to said common handle, wherein turning said dial adjusts a distance between said compressor handle and said common handle and wherein locking said pivot locking knob locks said distance between said compressor handle and said common handle.

5. The surgical instrument of claim 1, wherein said reducer tube has cutouts to straddle a rod.

6. The surgical instrument of claim 1, wherein said inner diameter of said reducer tube further accommodates an extender sleeve.

7. The surgical instrument of claim 1, wherein said reducer tube has a non-threaded end for engaging a counter torque tube.

8. The surgical instrument of claim 1, further comprising:
a pivot locking knob coupled to said common handle, wherein locking said pivot locking knob locks said distance between said shaft and said reducer tube.

9. The surgical instrument of claim 1, further comprising a driver, wherein said distractor handle is part of said driver.

10. The surgical instrument of claim 1, further comprising a locking mechanism having a first portion, a second portion, and a lock, wherein said first portion and said second portion are attachable to said distractor handle and said common handle.

11. The surgical instrument of claim 10, wherein said locking mechanism is a surgical ratchet.

12. The surgical instrument of claim 1, wherein a ratchet arm is coupled to said common handle to ratchet with said distractor handle.

13. A surgical instrument, comprising:
a reducer knob having a first passage through which a first shaft of a driver is acceptable, wherein a reducer tube is coupled to said reducer knob;

a connecting element coupled to said reducer knob and having a second passage through which said first shaft of said driver is acceptable:

a compressor handle coupled to said connecting element at a first end and having a through hole; and a common handle coupled to said compressor handle via said through hole, said common handle pivoting between said reducer knob and said compressor handle.

14. The surgical instrument of claim 13, wherein said compressor handle has an L-shape.

15. The surgical instrument of claim 13, wherein said through hole has an elongated shape that allows said common handle to travel a distance along a longitudinal axis, further comprising:
a dial coupled to said compressor handle for adjusting said distance; and a locking knob coupled to said common handle for locking said common handle at a desired position and angle.

16. The surgical instrument of claim 13, further comprising:
a locking mechanism coupled to said common handle for locking said common handle at a desired position and angle.

17. The surgical instrument of claim 13, further comprising:
a second shaft fixedly attached to or made part of said common handle, wherein moving said common handle towards said first shaft of said driver increases a distance between said second shaft and said reducer tube, wherein turning said reducer knob in a first direction extends a height of said reducer tube, wherein turning said reducer knob in a second direction retracts a portion of said reducer tube into said reducer knob, and wherein moving said common handle towards said compressor handle decreases said distance between said shaft and said reducer tube.

18. The surgical instrument of claim 17, wherein said reducer tube has cutouts to straddle a rod.

19. The surgical instrument of claim 17, wherein said reducer tube has an inner diameter that accommodates an extender sleeve.

20. The surgical instrument of claim 17, wherein said reducer tube has a non-threaded end for engaging a counter torque tube.

21. The surgical instrument of claim 13, wherein a ratchet arm is coupled to said first shaft to ratchet with said common handle.

22. The surgical instrument of claim 13, wherein said compressor handle has one or more weight reducing windows.

23. The surgical instrument of claim 13, wherein said common handle has one or more weight reducing windows.

* * * * *